(12) United States Patent
Woloszko (10) Patent No.: US 11,980,381 B2
(45) Date of Patent: May 14, 2024

(54) METHOD AND SYSTEM OF FLUID MANAGEMENT IN SURGICAL PROCEDURES

(71) Applicant: Smith & Nephew, Inc., Memphis, TN (US)

(72) Inventor: Jean Woloszko, Austin, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 1017 days.

(21) Appl. No.: 15/776,364

(22) PCT Filed: Nov. 21, 2016

(86) PCT No.: PCT/US2016/063049
§ 371 (c)(1),
(2) Date: May 15, 2018

(87) PCT Pub. No.: WO2017/095679
PCT Pub. Date: Jun. 8, 2017

(65) Prior Publication Data
US 2020/0164118 A1    May 28, 2020

Related U.S. Application Data

(60) Provisional application No. 62/262,596, filed on Dec. 3, 2015.

(51) Int. Cl.
*A61B 17/32* (2006.01)
*A61B 1/00* (2006.01)
(Continued)

(52) U.S. Cl.
CPC .. *A61B 17/320016* (2013.01); *A61B 17/1664* (2013.01); *A61B 17/1675* (2013.01);
(Continued)

(58) Field of Classification Search
CPC ..... A61B 1/00009; A61B 1/126; A61B 1/015; A61B 1/317; A61B 17/320016;
(Continued)

(56) References Cited

U.S. PATENT DOCUMENTS 3,835,842 A * 9/1974 Iglesias ............... A61B 1/12
600/105
3,850,175 A * 11/1974 Iglesias ............... A61B 1/12
606/46
(Continued)

FOREIGN PATENT DOCUMENTS

EP    2368484 A1 *  9/2011 ............ G06F 19/00
EP    2368484 A1     9/2011

OTHER PUBLICATIONS

International Search Report dated Feb. 13, 2017 for PCT application No. PCT/US2016/063049 filed Nov. 21, 2016; 6 pages.
(Continued)

*Primary Examiner* — Scott J Medway
(74) *Attorney, Agent, or Firm* — Dickinson Wright, PLLC; Mark E. Scott (57) ABSTRACT

Fluid management in surgical procedures. At least some of the illustrative embodiments are methods including: supplying fluid to a surgical site inside a patients body, drawing fluid from the surgical site through a first instrument by a first pump at a first flow rate, the first flow rate during the drawing responsive to expected or actual visibility within the surgical site; and then performing a surgical resection within the surgical site using the first instrument, the performing the surgical resection changes the first flow rate; and adjusting, by a fluid management system after the surgical resection, the first flow rate responsive to the expected or actual visibility within the surgical site.

30 Claims, 5 Drawing Sheets

(51) Int. Cl.
*A61B 1/015* (2006.01)
*A61B 1/317* (2006.01)
*A61B 17/00* (2006.01)
*A61B 17/16* (2006.01)
*A61B 18/00* (2006.01)
*A61B 18/12* (2006.01)
*A61B 18/16* (2006.01)
*A61M 1/00* (2006.01)
*A61M 3/02* (2006.01)

(52) U.S. Cl.
CPC ...... *A61B 17/1682* (2013.01); *A61B 17/1684* (2013.01); *A61B 17/1686* (2013.01); *A61B 17/32002* (2013.01); *A61M 1/77* (2021.05); *A61M 1/82* (2021.05); *A61M 3/0241* (2013.01); *A61M 3/0258* (2013.01); *A61B 1/00009* (2013.01); *A61B 1/015* (2013.01); *A61B 1/317* (2013.01); *A61B 2017/00544* (2013.01); *A61B 2017/00973* (2013.01); *A61B 2018/00577* (2013.01); *A61B 2018/1253* (2013.01); *A61B 2018/126* (2013.01); *A61B 2018/1266* (2013.01); *A61B 18/16* (2013.01); *A61B 2217/005* (2013.01); *A61B 2217/007* (2013.01); *A61M 2205/3334* (2013.01)

(58) Field of Classification Search
CPC ........ A61B 2217/005; A61B 2217/007; A61B 2218/002; A61B 2218/007; A61M 1/0058; A61M 3/0241; A61M 3/0258; A61M 3/0283; A61M 5/14228; A61M 2205/331; A61M 2205/3334
See application file for complete search history.

(56) References Cited

U.S. PATENT DOCUMENTS

| | | | |
|---|---|---|---|
| 4,662,871 A * | 5/1987 | Rafelson | A61M 1/0023 600/104 |
| 5,176,629 A | 1/1993 | Kullas et al. | |
| 5,254,117 A * | 10/1993 | Rigby | A61B 18/1482 606/42 |
| 5,423,738 A * | 6/1995 | Robinson | A61M 1/3612 604/6.01 |
| 5,556,378 A | 9/1996 | Storz et al. | |
| 5,630,798 A * | 5/1997 | Beiser | A61B 1/00135 604/66 |
| 5,882,339 A | 3/1999 | Beiser et al. | |
| 6,017,316 A * | 1/2000 | Ritchart | A61B 10/0283 600/565 |
| 6,258,111 B1 * | 7/2001 | Ross | A61B 17/32002 606/171 |
| 6,396,583 B1 * | 5/2002 | Clare | A61M 3/022 356/436 |
| 8,992,463 B2 * | 3/2015 | Hogard | A61M 1/28 604/29 |
| 2002/0026946 A1 | 3/2002 | McKay | |
| 2003/0236488 A1 | 12/2003 | Novak | |
| 2004/0220519 A1 * | 11/2004 | Wulfman | A61M 1/0084 604/93.01 |
| 2006/0122556 A1 * | 6/2006 | Kumar | A61B 1/015 604/67 |
| 2006/0122557 A1 | 6/2006 | Kumar et al. | |
| 2006/0129099 A1 * | 6/2006 | Kumar | A61M 3/0258 604/151 |
| 2007/0021713 A1 * | 1/2007 | Kumar | A61M 3/0229 604/27 |
| 2007/0078370 A1 * | 4/2007 | Shener | A61M 3/022 604/8 |
| 2007/0239113 A1 | 10/2007 | Reznik | |
| 2007/0249993 A1 | 10/2007 | Mollstam et al. | |
| 2008/0091061 A1 | 4/2008 | Kumar et al. | |
| 2008/0214994 A1 | 9/2008 | Guignard | |
| 2008/0234674 A1 * | 9/2008 | McClurken | A61B 18/148 606/50 |
| 2008/0243054 A1 | 10/2008 | Mollstam et al. | |
| 2008/0294095 A1 | 11/2008 | Zacharias | |
| 2010/0049119 A1 * | 2/2010 | Norman | A61M 3/022 604/31 |
| 2010/0076372 A1 * | 3/2010 | Hacker | A61B 17/32002 604/67 |
| 2010/0191178 A1 | 7/2010 | Ross et al. | |
| 2010/0280435 A1 * | 11/2010 | Raney | A61M 1/0064 604/22 |
| 2011/0237880 A1 * | 9/2011 | Hamel | A61B 1/015 600/104 |
| 2012/0302976 A1 | 11/2012 | Locke et al. | |
| 2013/0267779 A1 * | 10/2013 | Woolford | A61M 3/0258 600/156 |
| 2013/0267892 A1 * | 10/2013 | Woolford | A61M 3/0258 604/34 |
| 2013/0267894 A1 * | 10/2013 | Woolford | A61B 18/148 604/67 |
| 2014/0194871 A1 * | 7/2014 | Sanai | A61B 18/1445 606/41 |
| 2015/0025311 A1 | 1/2015 | Kadan et al. | |
| 2015/0164542 A1 | 6/2015 | Wulfman et al. | |
| 2015/0290387 A1 * | 10/2015 | Mollstam | A61M 13/006 604/24 |
| 2016/0136338 A1 * | 5/2016 | Lee | A47K 3/26 604/319 |
| 2017/0049952 A1 * | 2/2017 | Jezierski | A61M 3/022 |
| 2017/0112975 A1 * | 4/2017 | Fujisaki | A61M 1/0066 |
| 2017/0367729 A1 * | 12/2017 | Ginggen | A61B 17/205 |
| 2019/0029756 A1 * | 1/2019 | Natarajan | A61B 5/0036 |
| 2020/0367913 A1 * | 11/2020 | Forstein | A61B 90/06 |
| 2021/0038329 A1 * | 2/2021 | Pomati | G06F 3/013 |

OTHER PUBLICATIONS

Written Opinion dated Feb. 13, 2017 for PCT application No. PCT/US2016/063049 filed Nov. 21, 2016; 11 pages.
Chinese Application No. 201680081086.2 First Office Action and Text of First Office Action dated Oct. 29, 2019.
Chinese Application No. 201680081086.2 Search Report.
CN Second Office Action for Patent Application No. 201680081086.2 dated Jun. 15, 2020, 3 pages.

* cited by examiner

METHOD AND SYSTEM OF FLUID MANAGEMENT IN SURGICAL PROCEDURES

CROSS-REFERENCE TO RELATED APPLICATIONS

This application claims the benefit of U.S. Provisional Patent Application No. 62/262,596 filed Dec. 3, 2015 and titled "Method and System of Fluid Management in Surgical Procedures," incorporated by reference herein as if reproduced in full below.

BACKGROUND

Arthroscopic surgical procedures are procedures performed on a joint, such as a knee or shoulder, of a patient. In order to provide space within the joint to perform the procedure, the joint may be distended using a fluid (e.g., saline solution). However, resection procedures within a joint sometimes result in minor bleeding and create tissue fragments, which can cloud visibility within the joint. To maintain visibility, a continuous fluid flow through the joint may be employed. However, maintaining the pressure to distend the joint while simultaneously maintaining flow through the joint presents challenges.

BRIEF DESCRIPTION OF THE DRAWINGS

For a detailed description of exemplary embodiments of the invention, reference will now be made to the accompanying drawings in which.

DEFINITIONS

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Substantially the same" in relation to a recited value (e.g., flow rate from a surgical site) shall mean+/−10% of the recited value.

"Flow rate" in relation to linear or rotary peristaltic pumps shall mean average flow rate over a period of time (e.g., 0.5 to 2 seconds).

"Mechanical resection device" shall mean a surgical instrument that mechanically cuts or tears tissue at a surgical site, and draws tissue fragments and fluid through a channel in the mechanical resection device.

"Ablation device" shall mean a surgical instrument that volumetrically reduces and/or disassociates tissue by exposing the tissue to plasma of electrically charged particles. The ablation device draws tissue fragments and fluid through a channel in the ablation device.

"Pump system" shall mean a fluid pump, a source of mechanical motion coupled to the fluid pump, and an electrical and/or electromechanical system configured to control the speed of the fluid pump. For example, a pump system may include a peristaltic pump, an electric motor coupled to the peristaltic pump, a motor speed control circuit electrically coupled to the electric motor, and/or a transmission that controls the speed of the rotational energy form the motor provided to one or more pumps.

"Surgical resection" shall mean the disassociation of tissue from the patient. The disassociation shall include mechanical disassociation (e.g., cutting and burring) as well as electrical-based disassociation (e.g., electrical-current based cutting or desiccation, and plasma-based disassociation).

"Tissue" shall mean an aggregate of similar cells, cell products, and tissue matrix forming a structure or layer. Thus, tissue shall include but not be limited to bone, cartilage, muscle, tendons, and meniscus.

"Actual visibility" within a surgical site shall mean an indication of debris, disassociated tissue, blood, and/or gas bubbles within the fluid at the surgical site, with lower visibility indicating more debris, disassociated tissue, blood, etc., and higher visibility indicating less debris, disassociated tissue, blood, etc.

"Expected visibility" shall mean current expected visibility, or future expected visibility taking into account other factors (such as time, and type and aggressiveness of surgical resection).

"Controller" shall mean a field programmable gate array (FPGA), application specific integrated circuit (ASIC), programmable logic device (PLD), programmable logic controller (PLC), microcontroller, specifically implemented process-based system, or combinations thereof configured to read electrical signals and take control actions responsive to such signals.

"Set point" in relation to a flow rate for a resection shall mean a setting for operation of a resection device based on a type of resection device or a parameter used in operating the resection device (e.g., surgeon preferences).

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to fluid management during surgical procedures, such as arthroscopic procedures. More particularly, various embodiments are directed to active and automatic control of fluid pumps creating fluid flow through a surgical site in the patient's body. In situations where a single instrument provides outflow from the surgical site and the single instrument is being used for surgical resection the fluid flow is based on fluid flow to support the surgical resection (possibly to the detriment of visibility within the surgical site). After a surgical resection ceases, the fluid flow through the surgical site is controlled based on the visibility within the surgical site, taking into account the type of resection implement. In other cases, multiple instruments may be in fluid communication with the surgical site. In the multiple instruments case, during periods of time when one of the instruments is being used for surgical resection, the fluid flow through the instrument used for surgical resection is controlled based on fluid flow to support the resection and fluid flow through the remaining instruments is modulated responsive to visibility within the surgical site, which again may take into account the type of resection implemented by the first instrument used for surgical resection. After the surgical resection ceases, the fluid flow through the surgical site is controlled based on visibility within the surgical site, again possibly taking into account the type of resection implemented by the first instrument used for surgical resection that just ceased. The description starts with an example system shown in FIG. 1.

Figure 1:
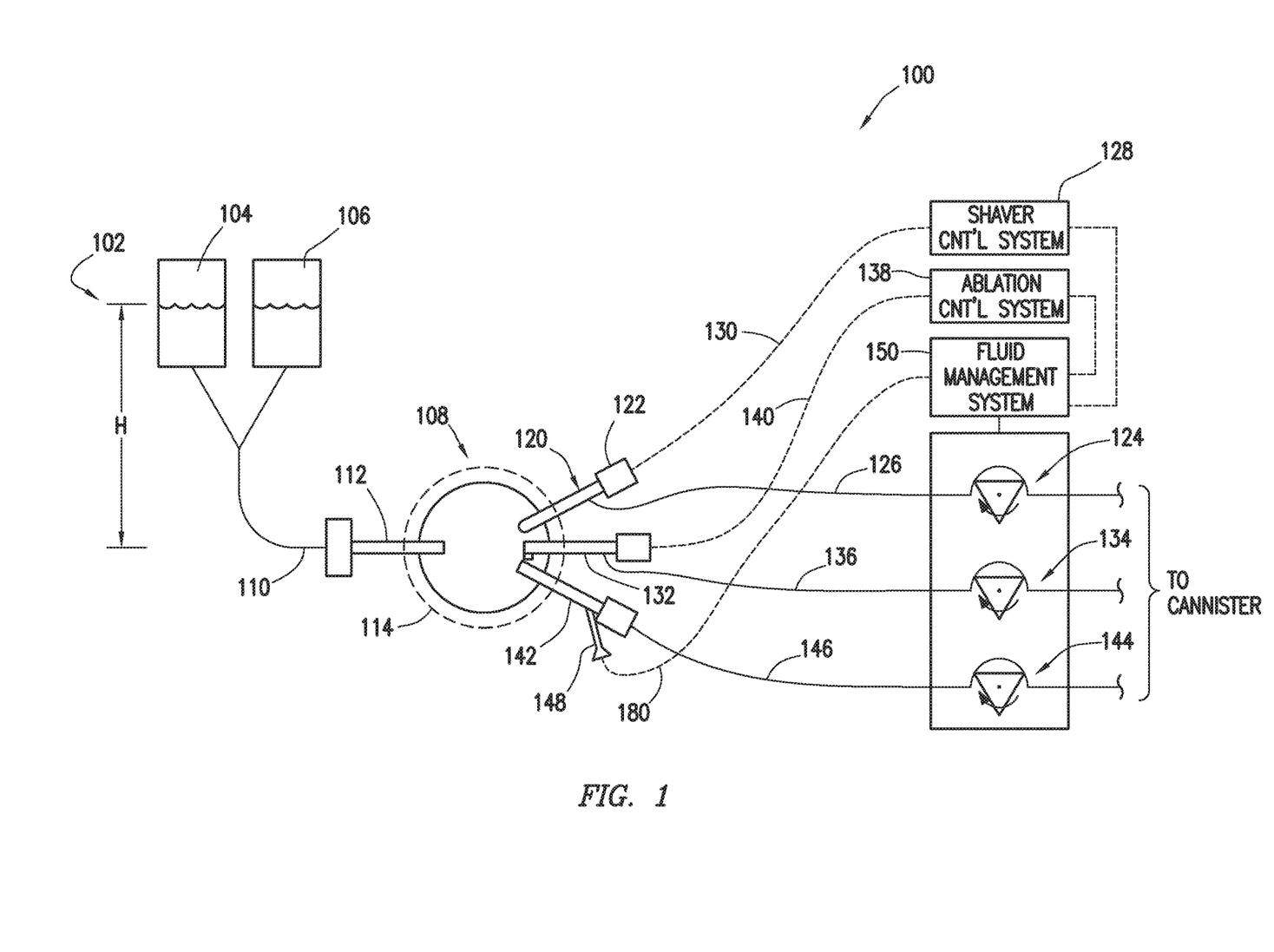
FIG. 1 shows a system in accordance with at least some embodiments.

FIG. 1 shows a surgical system 100 in accordance with at least some embodiments. In particular, FIG. 1 shows a source of fluid 102 in the form of saline bags 104 and 106 fluidly coupled to and providing a flow of fluid to a surgical site 108. While two saline bags 104 and 106 are shown, one or more may be used, such as by the saline bags hanging on a stand at a predetermined height H above the surgical site 108, where the height H (in combination with other factors, such as pressure drop across tubing 110) controls the pressure of fluid within the surgical site 108. In example systems, the fluid is provided to the surgical site by an instrument in the form of inflow cannula 112 having an internal channel fluidly coupled to the surgical site 108. The pressure of fluid within the surgical site may distend the surgical site slightly, such as shown by the dashed line 114 around the surgical site 108. The amount of distention will vary with pressure as well as the rigidity of the tissue surrounding the surgical site. The surgical site may be, for example, a knee, a shoulder, a hip, an ankle, or a wrist of the patient.

The example surgical system 100 further comprises a plurality of instruments associated with the surgical site out which fluid may flow. While the various embodiments are applicable to any instrument out which fluid may flow, the example surgical system 100 comprises a first instrument in the form of a mechanical resection device 120, such as a burr device, or a device known as a "shaver." So as not to unduly complicate the disclosure, the mechanical resection device 120 will be referenced as shaver 120 with the understanding that any mechanical resection device meeting the definition above may be used. The example shaver 120 may comprise a tubular member that defines an internal channel in fluid communication with a distal opening, and a mechanical blade within the tubular member and in operational relationship to the distal opening. The mechanical blade may be turned or oscillated by a motor (e.g., a motor within handle 122). The shaver 120 may be fluidly coupled to a pump 124 (shown as a peristaltic pump) by way of tubing 126, and may be electrically coupled to a shaver control system 128 by way of an electrical connection 130 (electrical connection shown in dashed lines to avoid confusion with tubular connections). In operation, the shaver control system 128 provides electrical energy to the motor in the handle 122, which motor oscillates or turns the mechanical blade at the distal tip. The mechanical blade and distal opening may be placed proximate to tissue to be removed or resected, and the mechanical blade motion may cut the tissue and thereby create tissue fragments. Moreover, the tissue fragments and fluid within the joint may be drawn through the channel inside the shaver 120 by way of pump 124.

Another example instrument that may be used is an ablation device, shown as example ablation device 132. The ablation device 132 may comprise a tubular member that defines an internal channel in communication with a distal opening, and a metallic electrode proximate to the distal opening. Upon application of electrical energy to the metallic electrode, a vapor layer followed by a plasma may form. The ablative device 132 may be fluidly coupled to a pump 134 (shown as a peristaltic pump) by way of tubing 136, and may be electrically coupled to an ablation control system 138 by way of an electrical connection 140 (shown with a dashed line). In operation, the ablation control system 138 provides electrical energy to the metallic electrode, which may create a vapor layer and subsequent plasma near the metallic electrode. The metallic electrode and distal opening may be placed proximate to tissue to be removed or resected, and the plasma may volumetrically reduce and/or disassociate the tissue, creating tissue fragments and ablation by-products. Moreover, the tissue fragments, ablation by-products, and fluid within the surgical site may be drawn through the channel inside the ablation device 132 by way of pump 134.

Before proceeding, it is noted that while theoretically possible to have both a shaver 120 and ablation device 132 inserted into the surgical site 108 at the same time, in many cases only one such instrument can or will be used at any given time, and thus it is possible that a single entry point through the patient's skin into the surgical site 108 may be created and used for both the example classes of instruments. The instrument the surgeon chooses to use may be inserted into the entry point, used within the surgical site 108, and then withdrawn such that the second instrument can be inserted and used. The fluid control aspects of such a procedure are discussed more below.

Still referring to FIG. 1, another example instrument that may be used is an outflow cannula 142. The outflow cannula 142 may comprise a tubular member that defines an internal channel in communication with a distal opening. The outflow cannula may fluidly couple to pump 144 (shown as a peristaltic pump) by way of tubing 146. Thus, the outflow cannula 142 may be used to ensure fluid flow through surgical site 108. Although there are many alternatives to the surgical system 100 of FIG. 1 (some alternatives discussed more below), in some cases the outflow cannula 142 may also comprise optics for visualizing the inside of the surgical site, the optics illustrated by eyepiece 148 associated with the outflow cannula 142. In other example systems, the optics may be associated with the inflow cannula 112, and the outflow cannula 142 may be omitted or, if used, not have optics for visualization. In yet still other cases, inflow and outflow may through a single cannula (with the inflow and outflow channels separated).

For purposes of explanation consider that fluid management system 150 receives an indication of actual visibility within the surgical site, receiving the indication of actual visibility within the surgical site is illustrated in FIG. 1 by communicative connection 180. While the communicative connection 180 is shown between the eyepiece 148 and a fluid management system 150, the connection is conceptual, as creating and sending the indication of actual visibility within the surgical site to the flow management system 150 may take many forms. For example, a camera may be coupled to the eyepiece, and a computer system may analyze the images from the camera and generate the indication of actual visibility. In yet still other cases, the indication of actual visibility within the surgical site may be created by devices associated with outflow tubing (e.g., 126, 136, 146) that measure turbidity and/or blood content of the fluid in one more optical wavelengths.

Still considering the example surgical system 100 of FIG. 1, it may be desirable to not only maintain a particular pressure within the surgical site 108 to achieve the distention, but also to provide fluid flow through the surgical site 108 to ensure that blood and tissue fragments are removed such that visibility (actual or expected, discussed more below) within the surgical site can be maintained. In accordance with example systems, the fluid management system 150 is communicatively coupled to the pump systems that include pumps 124, 134, and 144. The fluid management system 150 is also communicatively coupled to the example shaver control system 128 and the ablation control system 138. Through these example communicative connections, the fluid management system regulates the fluid flow through the surgical site 108 by coordination of the control of the various pump systems, with the primary control strategy being to ensure expected or actual visibility while reducing fluid usage, as such fluids may be a significant cost in the overall cost of a surgical procedure. Thus, if actual visibility within the surgical site is below a predetermined threshold (or expected visibility is low), the fluid management system 150 increases flow rate through surgical site (using one or all the possible pumps associated with the outflow devices, and discussed more below). Likewise, if actual visibility within the surgical site is at or above the predetermined threshold (or expected visibility is high), the fluid management system 150 decreases flow rate through surgical site (using one or all the possible pumps associated with the outflow devices, and discussed more below), including decreasing flow to zero (not taking into account leaks from the surgical site, which the fluid management system 150 cannot control). The example control philosophy will be explained through a series of example scenarios first based on the fluid management system receiving an indication of actual visibility.

Consider a first situation where there is no fluid flow through the shaver 120. No fluid flow may be because the pump 124 is off, or because the shaver is not in use and the mechanical blade has stopped in a position that blocks the aperture at the distal end of the shaver 120. In this first situation, also consider that there is no flow through ablation device 132 because the ablation device 132 is not in use and the pump 134 is off. Thus, in accordance with example systems, the fluid management system 150 may run pump 144 at a particular speed based on the actual visibility within the surgical site, and thus fluid flow to ensure actual visibility within the surgical site flows through the outflow cannula 142. It is noted that pump speed changes, even those to address visibility within the surgical site, are implemented relatively slowly in order to reduce the chances of collapse of the distention of the surgical site 108.

Now consider that the surgeon uses the shaver 120. In use, the shaver control system 128 provides electrical energy to a motor which results in movement of the mechanical blade. Moreover, the shaver control system 128 may activate the pump 124 (such as by communication with the fluid management system 150) such that the pump 124 provides a fluid flow rate through the shaver 120 commensurate with use of the shaver 120. For example, a certain fluid flow rate through the shaver 120 may be used to reduce the likelihood of clogging. In the example systems, the fluid management system 150 thus increases the pump 124 speed (in this case from a zero speed), leaves pump 134 off, and simultaneously modulates the speed of pump 144 based on the indication of actual visibility within the surgical site. In cases where the flow through the shaver 120 is sufficient to also maintain visibility within the surgical site, the speed of pump 144 may be reduced (including reduction to zero speed, and thus no flow). On the other hand, if the surgical resection implemented by the shaver 120 results in reduced visibility within the surgical site, the fluid management system 150 may increase the pump 144 speed (and since operation of the shaver 120 may be somewhat independent of flow through the shaver 120, increase the pump 124 speed) in an attempt to improve actual visibility within the surgical site. Again it is noted that pump speed changes, including speed changes for use during surgical resection, are implemented relatively slowly in order to reduce the chances of collapse of the distention of the surgical site 108.

The tubing between the shaver 120 and the pump 124 may be on the order of nine to twelve feet in length. Once the surgeon has removed or resected the particular tissue, the tissue fragments take a finite amount of time to travel to the pump 124 and ultimately to the disposal canister (not shown). Thus, even though the surgeon may stop energy flow to the motor in the handle 122, the shaver control system 128 and/or the fluid management system 150 may leave the pump 124 running for a predetermined period of time (e.g., 15 seconds) to ensure no or very few tissue fragments remain in the tubing 126 to reduce the likelihood of clogging. In some cases, the predetermined period of time may be a function of the flow rate through the pump such that at least the volume of tubing between the device and the pump is cleared by the pump. Once the predetermined period of time has passed, the pump 124 speed may be reduced (and in some cases reduced to zero). Simultaneously with the reduction in pump 124 speed, the fluid management system 150 modulates pump 144 responsive to actual visibility within the surgical site 108. For example, if the flow rate through pump 124 to reduce the possibility of clogging was more than was needed with respect to control of visibility within the surgical site, once pump 124 speed is reduced pump 144 may increase, yet not fully replace the flow formerly moving through pump 124. On the other hand, if the flow rate through pump 124 to reduce the possibility of clogging was less than was needed with respect to control of visibility within the surgical site, once pump 124 speed is reduced pump 144 may increase to replace the flow rate formerly moving through pump 124. Further still, if the flow rate through pump 124 to reduce the possibility of clogging is precisely that needed with respect to control of visibility within the surgical site, once pump 124 speed is reduced pump 144 may increase speed to fully replace the flow rate formerly moving through pump 124.

Consider again the first situation where there is no fluid flow through the shaver 120, and no flow through ablation device 132. Thus, to maintain visibility within the surgical site 108, the fluid management system 150 may run pump 144 at a particular speed, and thus a particular flow rate of fluid through the outflow cannula is maintained (including a zero flow depending on actual visibility). Now consider that the surgeon uses the ablation device 132. In use, the ablation control system 138 provides electrical energy to the metallic electrode which results in the formation of plasma. Moreover, the ablation control system 138 may activate the pump 134 (such as by communication with the fluid management system 150) such that the pump provides a fluid flow rate through the ablation device 132 commensurate with use. The fluid flow rate through the ablation device 132 may be a function of intended use of the ablation device 132. For example, for some types of tissue resection (e.g., treatment of delicate structures like cartilage, or meniscal fine sculpting), a relatively low flow rate may be used. For more aggressive procedures (e.g., bulk removal of tissue or bone spurs), higher flow rate may be used. In the example systems, the fluid management system 150 thus increases the pump 134 speed (in this case from a zero speed), leaves pump 124 off, and modulates the speed of pump 144 to maintain actual visibility within the surgical site. Moreover, as the surgeon changes modes of use of the ablation device 132, differing flow rates are used, and thus with each change of fluid flow rate through the ablation device 132 (i.e., with each change of pump 134 speed), the fluid management system 150 may make corresponding changes in the pump 144 speed to maintain actual visibility within the surgical site. In the case of ablation device 132, the flow rate through the device may be controlled based on the type of resection (as noted above), and in some cases the flow rate that enables a particular type of resection may be (initially at least) above the flow rate needed to maintain the actual visibility within the surgical site. In such situations then, modulation of pump 144 speed includes reducing pump speed to zero (and thus zero flow). Stated otherwise, the flow rate through the ablative device 132 (and the flow rate the surgical site) may be above that needed for maintaining actual visibility within the surgical site, and in such situations the higher flow rate controls.

The tubing 136 between the ablation device 132 and the pump 134 may be on the order of nine to twelve feet in length. Once the surgeon has removed or resected the particular tissue, the tissue fragments take a finite amount of time to travel to the pump 134 and ultimately to the disposal canister (not shown). Moreover, use of an ablation device 132 creates heat, and thus fluid flow may be continued after the ablation stops to cool the ablation device 132 and possibly the surrounding tissue. Thus, even though the surgeon may stop energy flow to the metallic electrode, the ablation control system 138 and/or the fluid management system 150 may leave the pump 134 running at a predetermined speed (and thus a predetermined flow rate) for a predetermined period of time (e.g., 30 seconds to five minutes) to ensure the ablation device is cool and to ensure no or very few tissue fragments are left in the tubing 136. During the period of time when the flow rate is maintained after use, the fluid management system may modulate pump 144 speed responsive to actual visibility within the surgical site. The flow rate through ablative device 132 after the energy flow has stopped may be above that needed for maintaining visibility within the surgical site, and in such situations the higher flow rate controls. Once the predetermined period of time has passed, the pump 134 speed may be reduced (and in some cases reduced to zero). Simultaneously with the reduction in pump 134 speed, the fluid management system 150 modulates pump 144 speed again responsive to actual visibility within the surgical site (including zero speed and thus zero flow).

The various embodiments discussed to this point have assumed that the flow management system 150 receives a value indicative of actual visibility within the surgical site, and acts accordingly. However, in yet still further embodiments the flow management system controls fluid flow out of the surgical site in an open-loop sense based on expected visibility. That is, in such embodiments no actual measurement indicative of actual visibility is made; rather, the fluid management system 150 acts based on other information either measured or inferred. Not having systems present to measure visibility and provide values indicative of visibility may significantly reduce the cost of the equipment associated with a surgical procedure. For example, a mechanical resection device in the form a shaver has an outer tube with a cutting window defined therein, and an inner tube telescoped within the outer tube with a corresponding cutting window. The inner tube is rotated and periodically the windows align. When the windows align, fluid flow through the inner tube pulls tissue and debris into the cutting windows, and further relative rotation cuts or shears the tissue and traps the tissue within tubing. The point is, the amount of debris created by a mechanical shaver may be relatively low.

By contrast, a mechanical resection device in the form of a burr comprises an outer tube, an inner member telescoped within the outer tube, and a burr tip coupled to the inner member and extending beyond the outer tube. The burr tip is rotated at high speed while fluid is drawn into the outer tube from which the burr tip protrudes. The inner member and the burr tip are rotated about the shared central axis with the outer tube, and thus debris created by the burr is thrown tangentially from the burr tip (and effectively tangentially to the shared central axis). The point is, even with high flow being drawing into the outer tube, the debris created by use a burr is not immediately drawn into the device, and the use of the burr as a mechanical resection device creates more debris and bubbles, and has a greater adverse effect on visibility than use of shaver.

Ablation devices that remove tissue by interaction of the tissue with plasma may have several modes of operation, as discussed above, even for the same wand and electrode configuration. Some modes of operation may create more debris and bubbles (e.g., aggressive modes of ablation) and other modes of operation create less debris and bubbles (e.g., modes for fine sculpting). The point is that the amount of debris and bubbles created, and thus the effect of each mode on visibility, is dependent on the mode of operation.

With respect to the open-loop control regarding visibility, in the example surgical system 100 the fluid management system 150 adjusts outflow rate through various outflow paths based on expected visibility taking into the account the overall situation, such as the type of surgical resection being performed (e.g., mechanical- or electrical-based disassociation), the aggressiveness of the surgical resection (e.g., burr versus shaver, ablation for fine sculpting versus ablation for based aggressive tissue removal), and other factors such as length of time tissue resection has taken place. Like the "closed-loop" case where an indication of visibility within the surgical sight is measured, the various operational techniques in the open-loop expected visibility cases are shown by way of example situations.

Still referring to FIG. 1, consider another a first situation where there is no fluid flow through the shaver 120. No fluid flow may be because the pump 124 is off, or because the shaver is not in use and the mechanical blade has stopped in a position that blocks the aperture at the distal end of the shaver 120. In this first situation, also consider that there is no flow through ablation device 132 because the ablation device 132 is not in use and the pump 134 is off. Thus, in accordance with example systems, the fluid management system 150 may run pump 144 at a particular speed to maintain expected visibility when no surgical resections are taking place. In some cases, the pump 144 speed may be based on an amount of time since the last surgical resection has ended and the type and aggressiveness of the last surgical resection. For example, if the last surgical resection ended only seconds earlier, and was a type of surgical resection that lowers visibility (e.g., use of a burr, or aggressive plasma-based ablation), then the fluid management system 150 may provide an initially higher flow rate by way of pump 144. By contrast, if the last surgical resection ended only seconds earlier and was a type of surgical resection that has less effect on visibility (e.g., use of shaver, or ablation-based fine tissue sculpting), then the fluid management system 150 may provide an initially lower flow rate (i.e., lower than the immediately previous case) by way of pump 144.

Moreover, the expected visibility may also be a function of an amount of time the previous surgical resection took place. For example, if the surgeon performed tissue ablation for an extended period of time (e.g., five to 10 minutes), even for surgical resections that produce less debris and bubbles the expected visibility decreases over time, and thus when extended the surgical resection ends the expected visibility is low and the flow through the pump 144 is higher than for shorter spans of surgical resection (e.g., two seconds or less).

Regardless of the aggressiveness and/or the amount of time the previous surgical resection was performed, the longer the surgical system 100 can move fluid through the surgical site (without further surgical resection taking place), the higher the expected visibility will go, to the point that eventually the flow management controller 150 may reduce the flow to zero. It is noted that pump speed changes, even those to address visibility within the surgical site, are implemented relatively slowly in order to reduce the chances of collapse of the distention of the surgical site 108.

Now consider that the surgeon uses the shaver 120. In use, the shaver control system 128 provides electrical energy to a motor which results in movement of the mechanical blade. Moreover, the shaver control system 128 activates the pump 124 (such as by communication with the fluid management system 150) such that the pump 124 provides a fluid flow rate through the shaver 120 commensurate with use of the shaver 120. In the example systems, the fluid management system 150 thus increases the pump 124 speed (in this case from a zero speed), leaves pump 134 off, and simultaneously modulates the speed of pump 144 based on the expected visibility within the surgical site. In cases where the flow through the shaver 120 is sufficient to also maintain expected visibility taking into account the type of shaver 120 and time the shaver 120 has been in use, the speed of pump 144 may be reduced (including reduction to zero speed, and thus no flow). On the other hand, if the surgical resection implemented by the shaver 120 is expected to adversely affect visibility (e.g., shaver 120 is burr), the fluid management system 150 may increase the pump 144 speed in an attempt to improve expected visibility within the surgical site. Again it is noted that pump speed changes, including speed changes for use during surgical resection, are implemented relatively slowly in order to reduce the chances of collapse of the distention of the surgical site 108.

The tubing between the shaver 120 and the pump 124 may be on the order of nine to twelve feet in length. Once the surgeon has removed or resected the particular tissue, the tissue fragments take a finite amount of time to travel to the pump 124 and ultimately to the disposal canister (not shown). Thus, even though the surgeon may stop energy flow to the motor in the handle 122, the shaver control system 128 and/or the fluid management system 150 may leave the pump 124 running for a predetermined period of time (e.g., 15 seconds) to ensure no or very few tissue fragments remain in the tubing 126 to reduce the likelihood of clogging. In some cases, the predetermined period of time may be a function of the flow rate through the pump such that at least the volume of tubing between the device and the pump is cleared by the pump. Once the predetermined period of time has passed, the pump 124 speed may be reduced (and in some cases reduced to zero). Simultaneously with the reduction in pump 124 speed, the fluid management system 150 modulates pump 144 responsive to expected visibility within the surgical site 108. For example, if the flow rate through pump 124 to reduce the possibility of clogging was more than was needed with respect to control of expected visibility within the surgical site, once pump 124 speed is reduced pump 144 may increase, yet not fully replace the flow formerly moving through pump 124. On the other hand, if the flow rate through pump 124 to reduce the possibility of clogging was less than was needed with respect to control of expected visibility within the surgical site, once pump 124 speed is reduced pump 144 may increase to replace the flow rate formerly moving through pump 124. Further still, if the flow rate through pump 124 to reduce the possibility of clogging is precisely that needed with respect to control of visibility within the surgical site, once pump 124 speed is reduced pump 144 may increase speed to fully replace the flow rate formerly moving through pump 124.

Consider again the first situation where there is no fluid flow through the shaver 120, and no flow through ablation device 132. Thus, to maintain expected visibility within the surgical site 108, the fluid management system 150 may run pump 144 at a particular speed, and thus a particular flow rate of fluid through the outflow cannula is maintained (including a zero flow depending on the expected visibility). Now consider that the surgeon uses the ablation device 132. In use, the ablation control system 138 provides electrical energy to the metallic electrode which results in the formation of plasma. Moreover, the ablation control system 138 may activate the pump 134 (such as by communication with the fluid management system 150) such that the pump provides a fluid flow rate through the ablation device 132 commensurate with use. The fluid flow rate through the ablation device 132 may be a function of intended use of the ablation device 132. For example, for some types of tissue resection (e.g., treatment of delicate structures like cartilage, or meniscal fine sculpting), a relatively low flow rate may be needed. For more aggressive procedures (e.g., bulk removal of tissue or bone spurs), higher flow rate may be used. In the example systems, the fluid management system 150 thus increases the pump 134 speed (in this case from a zero speed), leaves pump 124 off, and modulates the speed of pump 144 to maintain expected visibility within the surgical site. Moreover, as the surgeon changes modes of use of the ablation device 132, differing flow rates are used, and thus with each change of fluid flow rate through the ablation device 132 (i.e., with each change of pump 134 speed), the fluid management system 150 may make corresponding changes in the pump 144 speed to address expected visibility within the surgical site. In the case of ablation device 132, the flow rate through the device may be controlled based on the type of resection (as noted above), and in some cases the flow rate that enables a particular type of resection may be (initially at least) above the flow rate needed to maintain the expected visibility within the surgical site. In such situations then, modulation of pump 144 speed includes reducing pump speed to zero (and thus zero flow). Stated otherwise, the flow rate through the ablative device 132 (and the flow rate the surgical site) may be above that needed for maintaining expected visibility within the surgical site, and in such situations the higher flow rate controls.

The tubing 136 between the ablation device 132 and the pump 134 may be on the order of nine to twelve feet in length. Once the surgeon has removed or resected the particular tissue, the tissue fragments take a finite amount of time to travel to the pump 134 and ultimately to the disposal canister (not shown). Moreover, use of an ablation device 132 creates heat, and thus fluid flow may be continued after the ablation stops to cool the ablation device 132 and possibly the surrounding tissue. Thus, even though the surgeon may stop energy flow to the metallic electrode, the ablation control system 138 and/or the fluid management system 150 may leave the pump 134 running at a predetermined speed (and thus a predetermined flow rate) for a predetermined period of time (e.g., 30 seconds to five minutes) to ensure the ablation device is cool and to ensure no or very few tissue fragments are left in the tubing 136. During the period of time when the flow rate is maintained after use, the fluid management system may modulate pump 134 speed responsive to expected visibility within the surgical site, again taking into account the amount of time of previous use of the ablation device 132, the aggressiveness of the use of the ablation device 132, and the amount of time since the ablation ended. The flow rate through ablative device 132 after the energy flow has stopped may be above that needed for maintaining expected visibility within the surgical site, and in such situations the higher flow rate controls. Once the predetermined period of time has passed, the pump 134 speed may be reduced (and in some cases reduced to zero). Simultaneously with the reduction in pump 134 speed, the fluid management system 150 modulates pump 144 speed again responsive to expected visibility within the surgical site (including zero speed and thus zero flow).

The various embodiments discussed to this point have assumed that the flow rate of fluid through the surgical site is based on the higher of the flow rate needed to support a particular device for surgical resection (e.g., a resection set point), or control of actual or expected visibility within the surgical site. However, the surgical system 100 may also implement a mode of operation where the rate of clearing the surgical site of excess tissue and blood is increased, sometimes referred to as a lavage mode. The lavage mode may be may be manual triggered by the surgeon, may take place during periods of time when no surgical procedures are taking place inside the surgical site, and may also take place while performing surgical procedures.

Consider first a situation where a surgical resection has just ceased (e.g., use of the shaver 120 has just stopped) and where visibility within surgical site is low. As discussed above, for a predetermined period of time the fluid flow rate through the instrument that performed the resection (e.g., the shaver 120 or the ablation device 132) may continue, and also fluid flow rate through the outflow cannula 142 may continue, with the fluid management system 150 automatically controlling the pump speeds. While eventually the surgical site 108 will be cleared based on the combination of the post-surgical resection flow rate and the flow rate specifically responsive to expected or actual visibility within the surgical site, the surgeon may elect to speed the process by increasing the fluid flow rate through the surgical site. The election by the surgeon may be conveyed to the fluid management system 150 in any suitable form, such as by pressing a button on the front panel of the fluid management system, pressing a foot-actuated switch communicatively coupled to the fluid management system 150, pressing a finger-actuated switch on the resection instrument (which is communicated to the fluid management system 150 by the respective control system (e.g., shaver control system 128, ablation control system 138)), or a button on the camera system. Regardless of the form in which the fluid management system 150 learns of the triggering of the lavage mode, the fluid management system 150 may increase the flow rate through the surgical site by increasing the pump speed of one or more of the pumps fluidly coupled to the surgical site 108. For example, the fluid management system 150 may increase the pump 144 speed associated with the outflow cannula 142 while maintaining the fluid flow rate through the resection instrument. In another example, the fluid management system 150 may increase the pump 144 speed and simultaneously increase the pump speed associated with the resection instrument (e.g., the shaver 120 or the ablation device 132). In yet still other cases (and in situations that allow), the fluid management system 150 may increase all the pump speeds to implement the lavage mode.

Ending the lavage mode may likewise take many forms. In some cases, triggering of the lavage mode (and thus the increased fluid flow rate) may take place for a predetermined period of time (e.g., 30 seconds to three minutes). In other cases, the lavage mode may end based on the visibility within the surgical site (e.g., as seen through the eyepiece 148 either by the surgeon, or by an automated system analyzing frames of video produced by a camera associated with the eyepiece 148). In yet still other cases, the lavage mode may end based on turbidity of the fluid within the tubing 126, 136, and/or 146 as measured by a light transmittance device. Regardless, once the lavage mode ends the fluid management system 150 reduces the pump speed of one or more pumps (including reducing speed to zero for some instruments) to return the pre-lavage mode fluid flow rates (which may include continuing post-resection flow through an instrument for some pumps, and continuing to modulate responsive to visibility within the surgical site for pump 144).

The specification now turns to a description of detection of whether instruments are within the surgical site (or have been removed from the surgical site), and operational aspects based on the determination. In particular, the example surgical system 100 has a shaver 120 and an ablation device 132. In the case of the shaver 120, a determination of whether the distal end of the shaver 120 is within the surgical site may take many forms. For example, when the blade of the shaver 120 is within the surgical site, a certain amount of torque may be needed from the motor in the handle to turn or oscillate the blade, and a lower torque may be needed if the blade is within the open air. Thus, in other cases the detecting that the shaver 120 is within the surgical site 108, or is not, may be made based on the energy draw of the motor within the handle (with higher torque equating to higher energy, and vice versa).

In the case of the ablation device 132, a determination of whether the distal end of the ablation device 132 is within the surgical site may be based on the electrical impedance measured between the metallic electrode and a return electrode (e.g., another metallic member on the ablation device 132 in the case of a bipolar device, or a grounding pad physically coupled to the patient in the case of a monopolar device). For example, when the ablation device 132 has its distal end within the surgical site 108, the metallic electrode is exposed to fluid in the surgical site, which fluid is conductive. However, when removed from the surgical site the metallic electrode is exposed to air, which is significantly less conductive than the fluid within the surgical site 108. Detecting that the ablation device 132 has been removed from the surgical site 108 may thus involve reading impedance measured between the metallic electrode and the return electrode.

Regardless of the detection mechanism for detecting that an instrument has been removed from operational relationship to the surgical site, once detected the flow rate of fluid associated with the instrument is reduced to zero. For example, if the shaver control system 128 detects that the shaver 120 has been removed from the surgical site 108, the shaver control system 128 may communicate the information to the fluid management system 150, and the fluid management system 150 may then reduce the flow rate of the first instrument to zero, and likewise modulate the flow rate associated with one or more remaining instruments (e.g., modulate the flow rate associated with the outflow cannula 142 and/or modulate the flow rate associated with a remaining instrument).

Moreover, the detection regarding whether a surgical instrument has been removed is equally useful in the opposite situation—detecting that an instrument has been placed in operational relationship to the surgical site. That is, by the same mechanisms discussed with respect to detecting removal from the surgical site, a determination may be made that an instrument has been inserted, and the fluid flows may be adjusted accordingly. For example, when the system detects that an instrument has been newly inserted, the fluid management system 150 may increase the flow rate associated with the newly inserted instrument (e.g., increase from zero) and likewise the fluid management system 150 may reduce the flow rate associated with the remaining instruments associated with the surgical site.

The various embodiments described with respect to FIG. 1 have assumed multiple instruments (120, 132, 142) associated with the surgical site 108. However, in some cases, and possibly to reduce not only the cost of the surgical procedure but also the number of entry points (e.g., to reduce scarring), only one instrument may be used and associated with outflow. Still referring to FIG. 1, consider that a surgeon elects to use the inflow cannula 112 (and in this example the inflow cannula houses the visualization system for the procedure), and that the surgeon creates a single entry point for the surgical instruments and thus uses the instruments one at a time. For example, the surgeon may initially use the ablative device 132, and during such time the ablative device 132 provides the only instrument-based outflow of fluid from the surgical site 108. Thus, when the ablative device 132 is inserted but not in use, the fluid management system 150 controls the pump 134 speed responsive to expected or actual visibility within the surgical site 108. The surgeon may then perform a surgical resection using the ablative device, and the outflow from the surgical site will be the flow in support of use of the ablative device 132. Thus, in this single instrument case, during the surgical resection the flow rate of fluid may be controlled based on the needs of resection device (possibly to the detriment of the visibility within the surgical site 108). Moreover, and as discussed above, even once the surgical resection has ended, the flow rate through the example ablative device 132 may continue for a predetermined period of time to clear the tubing and remove heat. However, once the predetermined period of time has elapsed after the surgical resection has ended, the fluid management system 150 may again modulate the example pump 134 responsive to expected or actual visibility within the surgical site 108. The modulation may include: increasing the flow rate responsive to the actual visibility within the surgical site being below a predetermined threshold; increasing the flow rate responsive to the expected visibility being low; decreasing the flow rate (including decreasing to zero) responsive to the visibility within the surgical site being at or above predetermined threshold; and decreasing the flow rate (including decreasing to zero) responsive to the expected visibility being high.

The surgeon may then remove the ablative device 132 (which can be sensed as described above), and then insert the example shaver 120 (also possibly sensed as above, and with the shaver control system 128 configured to stop the mechanical blade in an open configuration each time). In such a case, the flow management system 150 may then adjust the flow through the shaver 120 responsive to expected or actual visibility within the surgical site 108. Use of the shaver 120 in a surgical resection when the shaver 120 is the only outflow instrument operates similarly to the description of the ablative device 132, with the exception that the flow through the shaver 120 for any operational mode may only need to meet a minimum flow rate, and thus greater flow may be used if expected or actual visibility within the surgical site is low.

In the example systems of FIG. 1 the height H of the saline bags 104 and 106 above the surgical site 108 is the primary parameter that controls the fluid pressure within the surgical site 108. In such an example system then, the pressure within the surgical site 108 is largely controlled by the height H, and the flow rate through the surgical site is controlled by the pumps 124, 134, and 144 responsive to the fluid management system 150. However, implementing changes in pressure involve changing the height H of the saline bags 104 and 106. Moreover, such system does not automatically adjust the pressure to account for pressure drop across the tubing 110 (which pressure drop changes as a function of flow rate through the surgical site 108). Thus, the specification now turns to other illustrative embodiments that utilize an inflow pump.

Figure 2:
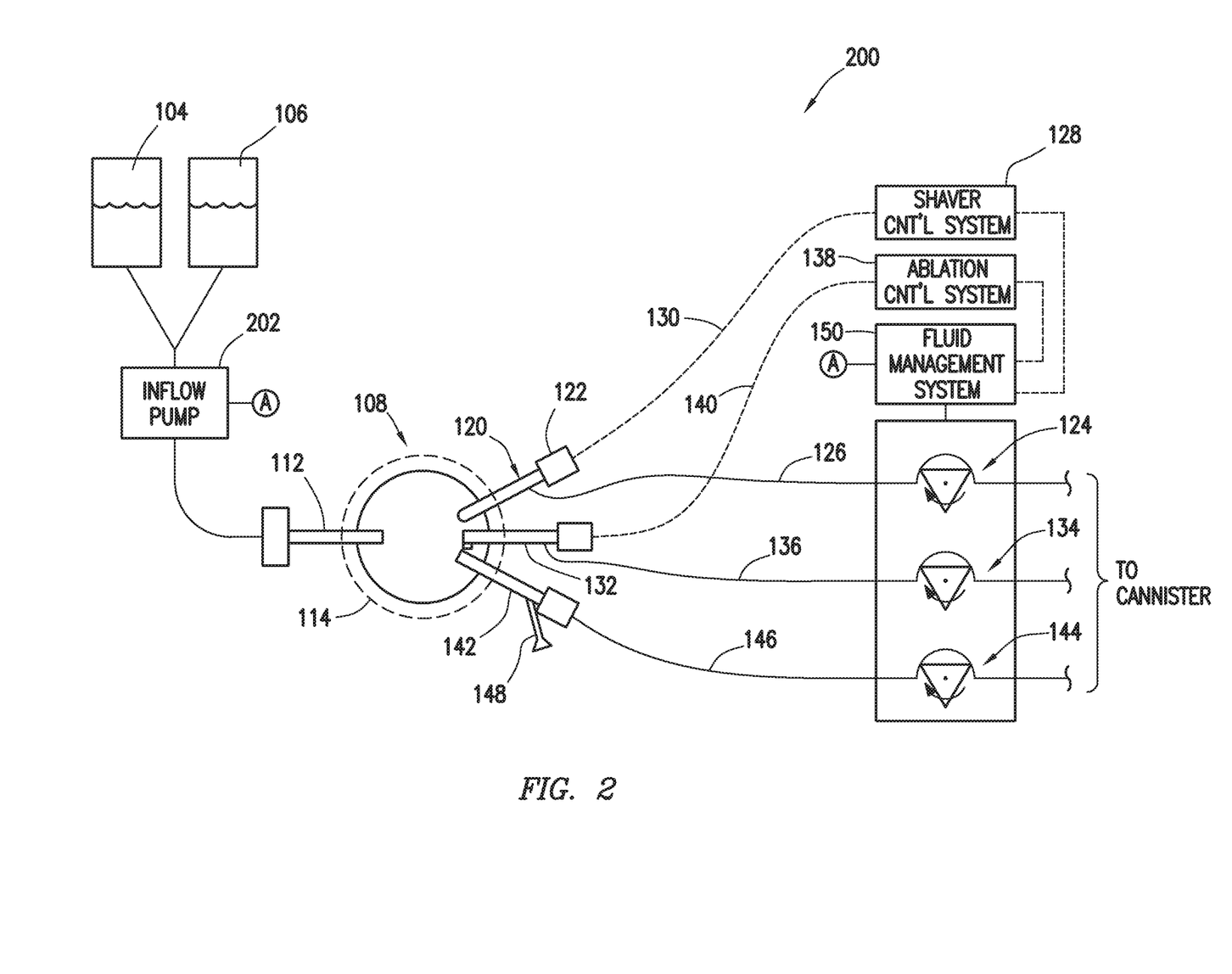
FIG. 2 shows a system in accordance with at least some embodiments.

FIG. 2 shows a surgical system 200 in accordance with other example embodiments. In particular, FIG. 2 shows a surgical system 200 similar to the surgical system 100 in many respects, and thus like components carry the same reference numbers. FIG. 2 can also be said to show a system where the fluid management system 150 operates without measuring actual visibility within the surgical site 108 (by the lack of communicative connection between the eyepiece 148), but systems with an inflow pump may be used with or without the measuring actual visibility. Unlike the surgical system of FIG. 1, however, the surgical system 200 also includes an inflow pump 202 which takes suction from saline bags 104 and 106, and its discharge is fluidly coupled to the surgical site 108. The inflow pump 202 may be communicatively coupled to the fluid management system (as shown by the balloon "A" connections) such that the fluid management system 150 may control operational aspects of the inflow pump 202. The fluid flow out of the surgical site through the example devices operates the same as discussed with respect to the surgical system 100 of FIG. 1, and will not be repeated here so as not to unduly lengthen the specification. The inflow pump 202 may take several forms. For example, the inflow pump may be a peristaltic pump similar to pumps 124, 134, and 144. In such systems, the inflow pump speed may be controlled responsive to increases and decreases in the flow rate through the surgical site 108 (the flow rates implemented across the two or more instruments and related pumps). For example, if the fluid management system 150 is modulating fluid flow rate through the surgical site 108 responsive to expected or actual visibility within the surgical site, the fluid management system 150 may correspondingly modulate the inflow pump speed. If the surgeon implements a lavage mode, the inflow pump speed may increase (along with outflow pump speed increases) to provide the higher flow rate through the surgical site 108, and then decrease speed (along with decreases in pump speed for pumps controlling outflow) once the lavage mode is complete.

Still considering the inflow pump as a peristaltic pump, changes in the pressure of the fluid within the surgical site 108 may be implemented by momentary changes in inflow pump speed. For example, when increased pressure is desired (and considering that outflow remains constant), a momentary increase in speed of the inflow pump provides additional volume that results in increased pressure. Oppositely, when decreased pressure within the surgical site is desired (and considering that outflow remains constant), a momentary decrease in speed of the inflow pump results in slightly lower volume that results in decreased pressure in the surgical site. It is also possible to implement increases and decreases in pressure within the surgical site 108 by keeping the inflow pump speed constant, and momentarily increasing or decreasing the total flow rate out of the surgical site 108. Another type of pump that may be used as inflow pump 202 is a linear peristaltic pump, which has no rotational components, but instead uses a series of pinch valves that open and close to mimic rotary peristaltic pump operation.

In yet still other cases, the inflow pump 202 may be a pump whose outlet pressure is a function of flow and speed of the rotor of the pump. For example, the inflow pump 202 may be a centrifugal pump. In such cases, for constant outflow, the pressure within the surgical site 108 may be controlled by pump speed. To maintain pressure within the surgical site 108 during changes in outflow, pump speed may be adjusted. For example, during lavage mode when outflow from the surgical site increases, to maintain pressure within the surgical site and therefore distention, the pump speed may need to be increased. When outflow is again reduced, in order to avoid over-pressuring the surgical site 108, the pump speed may need to be reduced.

Figure 3:
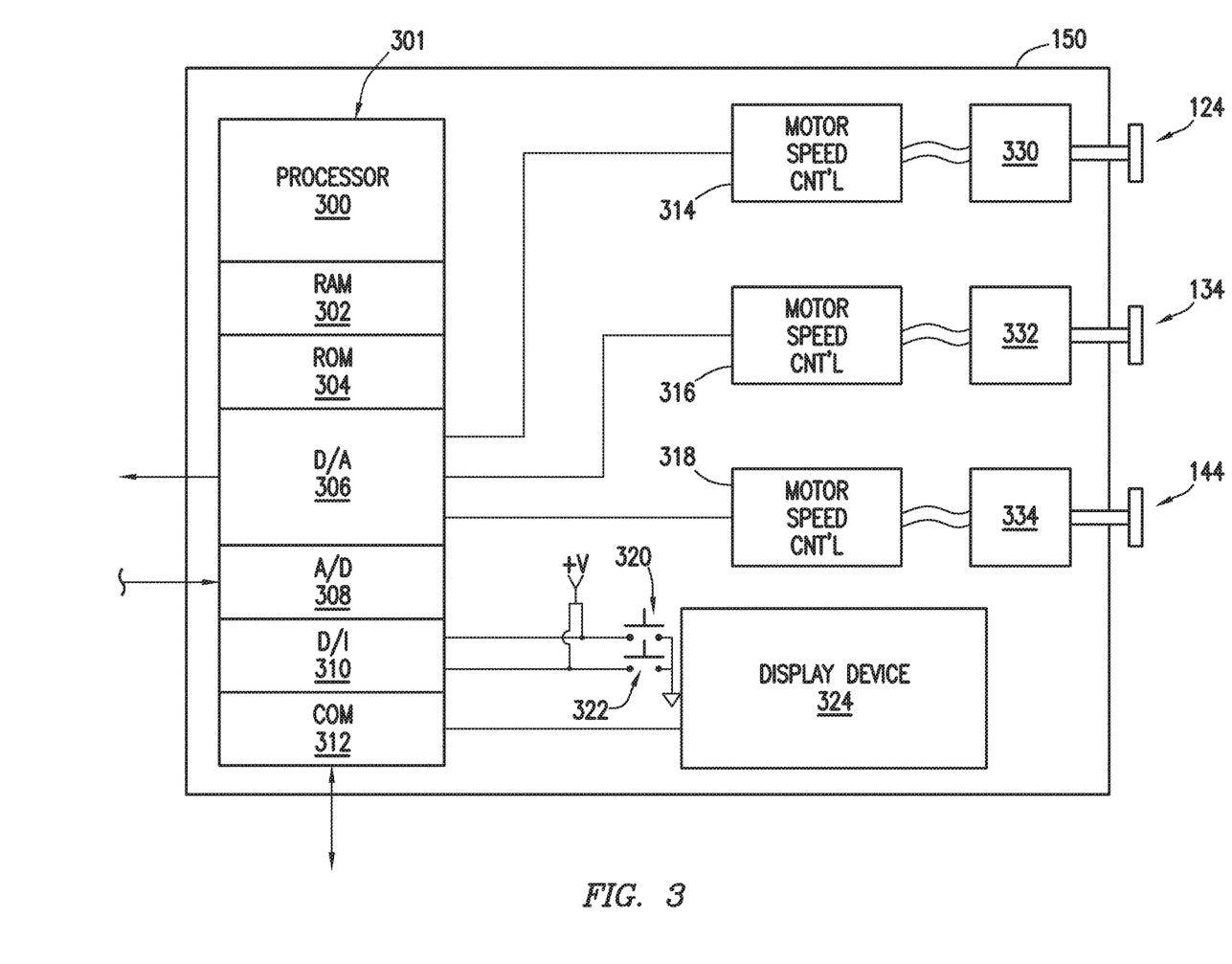
FIG. 3 shows a flow management system in accordance with at least some embodiments.

FIG. 3 shows, in block diagram form, an example fluid management system 150 in accordance with at least some embodiments. In particular, the example fluid management system 150 has a controller 301 coupled to various internal and external components. In the example system of FIG. 3, the controller 301 takes the example form of a microcontroller having processor 300 electrically coupled to random access memory (RAM) 302, read-only memory (ROM) 304, digital-to-analog (D/A) outputs 306, analog-to-digital (A/D) inputs 308, digital inputs (D/I) 310, as well as communication logic (COM) 312 sections. Though controller 301 is shown in the form of a microcontroller, in other cases individual components (i.e., an individual processor, RAM, ROM, etc.) may be combined to implement the functionality, or other devices such as FGPAs, ASICs, PLCs, and the like may be used. The example RAM 302 may be the working memory for the processor 300. ROM 304 may store programs and data in a non-volatile fashion, and the processor 300 may copy the programs and data from the ROM 304 to RAM 302 during execution of the programs. The digital-to-analog outputs 306 may be used to provide analog signals to other devices within the fluid management system, such as the motor speed controllers 314, 316, and 318 (discussed more below), or to external devices (e.g., a separate inflow pump controller, if used). The analog-to-digital inputs 308 may provide the controller 301 the ability to read analog signals, such as analog signals indicative of actual visibility within the surgical site, or analog indications of desired pump speeds from external devices (e.g., the shaver controller 128 or the ablation controller 138). The digital inputs 310 may be used to receive information into the controller 301, such as information from example push buttons 320 and 322 (discussed more below). Finally, the communication logic 312 may be used for packet-based communications with internal or external devices (e.g., a system that provides an indication of actual visibility within the surgical site, display device 324, or external the control systems). The individual devices through which the controller 301 receives information may be individually referred to as an input port, and collectively input ports.

Regardless of the mechanism by which the flow management system 150 receives the indication of visibility within the surgical site and other information, the controller 301 may implement the fluid flow by commanding one or more pumps that draw fluid flow through the surgical site. In the example system, the fluid management system 150 implements three peristaltic pumps 124, 134, and 144. As shown, the peristaltic pumps 124, 134, and 144 are each turned by motors 330, 332, and 334, respectively. The motors may take any suitable form. For example, the motors may be direct current (DC) electric motors, and thus the motor speed controllers 314, 316, and 318 provide a DC voltage to the electric motors which control the speed of the output shafts. In other cases, the motors may be alternating current (AC) electric motors, and thus the motor speed controllers 314, 316, and 318 provide an AC voltage at varying frequency to the electric motors which controls the speed of the output shafts. In yet still other cases, the motors may be pneumatic motors, and thus the motor speed controllers 314, 316, and 318 provide air at varying pressures, where the pressure controls the speed of the output shafts. Thus, regardless of the type of motor implemented, the motor speed controllers 314, 316, and 318 control the speed of the motors responsive to commands provided from the controller 301. While the commands to the motor speed controllers are shown to be analog signals, in other cases the motor speed controllers may receive commands in packet-based messages (e.g., through the communication logic 312). Finally, while the motors are shown to directly couple to the peristaltic pumps, in other cases various gears and/or belts may be used to transfer the rotational motion of the shaft of each motor to its peristaltic pump components. While FIG. 3 is based on having rotary peristaltic pumps, one having ordinary skill and with the benefit of this disclosure could modify the system to be used with other types of outflow pumps, such as linear peristaltic pumps.

Before proceeding, it is noted that the embodiments of FIG. 2 show the inflow pump 202 as an external device to the fluid management system 150; however, in other cases the inflow pump may be an integral component with the fluid management system, and thus additional motor speed control, motors, and pumps may be included. Moreover, while three motor speed controllers, motors, and pumps are shown in FIG. 3 (the combination of a motor speed controller, motor, and pump being an example of a pump system), the fluid management system may implement two or more depending on the number of instruments the fluid management system may support, and whether an inflow pump is used in the system. Finally, it is noted that the fluid management system may have greater capability than is used in any particular surgical procedure, and thus not all motor speed controllers, motors, and pumps may be used in every surgical procedure.

Figure 4:
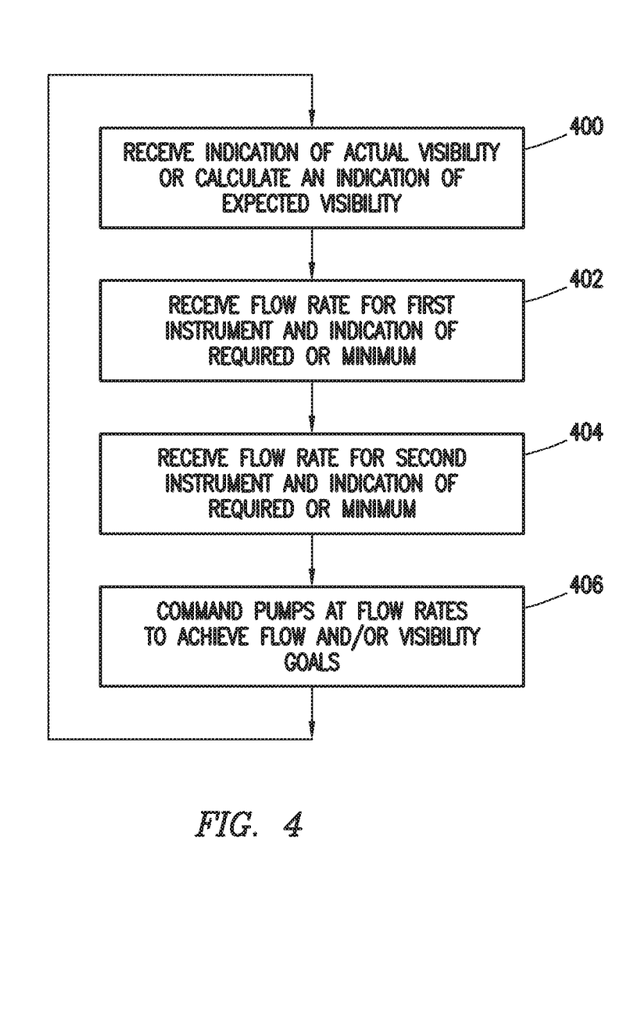
FIG. 4 shows a method in accordance with at least some embodiments.

FIG. 4 shows a flow diagram for operation of the controller 301 of the flow management system 150. For example, example processor 300 may execute a program that causes the processor to perform the recited steps. As another example, an ASIC may be designed and constructed to perform the recited steps. In the example method, the controller 301 receives an indication of actual visibility or calculates an indication of expected visibility within the surgical site (block 400). As discussed above, the indication of actual visibility within the surgical site may be provided from any of a variety devices and systems, such as from systems analyzing frames of video taken inside the surgical site or devices that measure turbidity of fluid within outflow tubing. The receiving too could take many forms, such as receiving an analog signal by the A/D inputs 308 (FIG. 3), or receiving a packet-based message over the communication logic 312 (also FIG. 3). In the case of calculating an indication of expected visibility, the controller 301 may take into account the various parameters discussed in the examples above.

The next step in the example method is receiving a flow rate for a first instrument along with an indication of whether the flow rate is a required flow rate, or a minimum flow rate for the instrument (block 402). Consider first the shaver 120. When the shaver 120 is in use, fluid flow through the shaver 120 carries tissue fragments and blood away from the surgical site; however, beyond ensuring proper flow through the tubing 126, operation of the shaver 120 may not be significantly affected by the flow rate above a minimum flow rate. Thus, in the case of the shaver 120, when the surgeon activates the shaver 120, the shaver control system 128 may send a flow rate to the fluid management system 150, which in turn activates the respective pump at the flow rate. The shaver control system 128 may also send an indication that the flow rate is a minimum flow rate, thus giving the flow management controller 150 the option and ability to increase the flow through the shaver 120 if needed, such as increases responsive to expected or actual visibility or increases when a lavage mode is triggered while the surgeon is still using the shaver.

With respect to the indication of required or minimum flow rate, consider next the ablation device 132. When the ablation device 132 is in use, fluid flow through the ablation device 132 carries tissue fragments, blood, and bubbles away from the surgical site; however, operation of the ablation device 132 may be dependent to a large extent on the flow rate through the ablation device, with more aggressive ablation taking place with higher flow rates (and possibly higher energy delivered to the plasma), and more docile ablation (e.g., smoothing operations) taking place with lower flow rates (and possibly lower energy delivered to the plasma). Thus, in the case of the ablation device, when the surgeon activates the ablation device, the ablation control system 138 may send a flow rate to the fluid management system 150, which in turn activates the respective pump at the flow rate. The ablation control system 138 may also send an indication that the flow rate is a required flow rate, thus constraining the fluid management system 150 to providing only the flow rate requested through the ablative device. In such a case, the fluid management system 150 could not, for example, increase the flow through the ablation device 132 even if the surgeon triggered a lavage mode while still using the ablation device.

The next step in the example method is receiving a flow rate for the second instrument along with an indication of whether the flow rate is a required flow rate, or just a minimum flow rate for the instrument (block 404), if a second instrument is present. It is assumed that if the fluid management system 150 receives a flow rate for an instrument of zero that the instrument is either no longer in operational relationship to the surgical site 108 (e.g., has been removed), or even if still in operational relationship is not in a configuration to enable fluid flow (e.g., the mechanical blade occluding the aperture of the shaver). Thus, any instrument for which the processor has received a flow rate of zero will not participate in providing outflow from the surgical site. While FIG. 4 only shows receiving flow rates and two surgical instruments, the example system would be operable receiving flow rates for one or more surgical instruments (as discussed above).

Next, the processor commands one or more pumps at various speeds to achieve the flow rates and/or expected or actual visibility goals (block 406). As discussed above, if only a single outflow channel is available, the processor commands the pump speed to achieve visibility goals (during periods of time when no surgical resection is taking place), or the processor commands the pump speed to achieve a flow rate responsive to a resection flow set point through the instrument (possibly to the detriment of visibility). If multiple outflow channels are available, then the flow rate through at least one outflow channel is modulated responsive to expected or actual visibility. In the example systems of FIGS. 1 and 2, the outflow cannula 142 is an instrument over which the fluid management system 150 has complete control, without influence from external devices or systems. The example method then retreats again to receiving an indication of visibility or calculating an indication of expected visibility (block 400), checking for flow rates for instruments received from other devices (blocks 402 and 404), and commanding the pumps at flow rates to achieve flow and/or visibility goals block 406), in a continuous loop.

Figure 5:
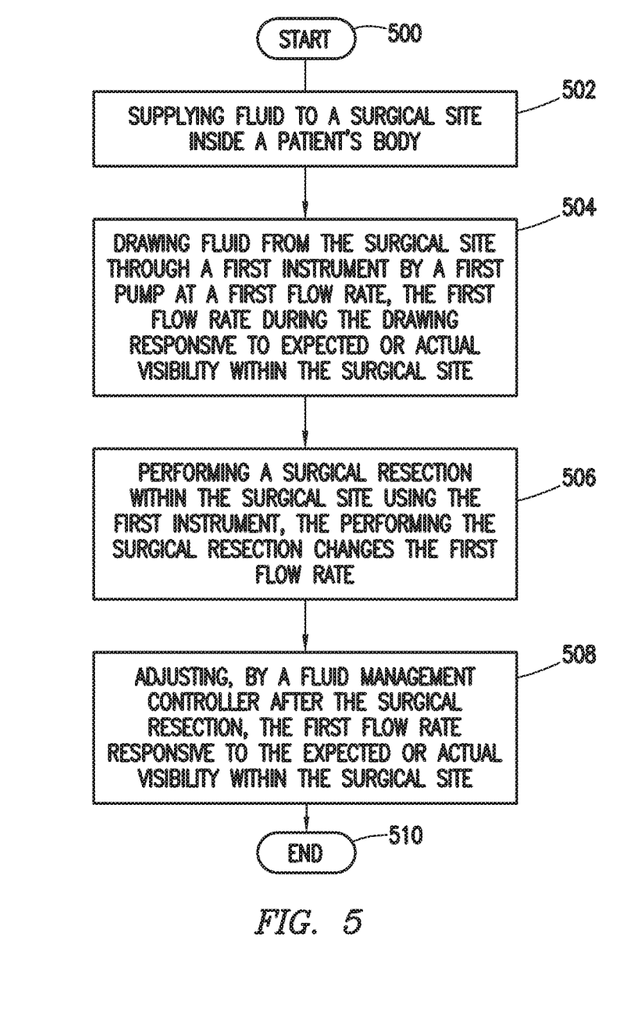
FIG. 5 shows a method in accordance with at least some embodiments.

FIG. 5 shows a method in accordance with at least some embodiments, at least a portion of which may be implemented using the fluid management system. In particular, the method starts (block 500) and proceeds to: supplying fluid to a surgical site inside a patient's body (block 502); drawing fluid from the surgical site through a first instrument by a first pump at a first flow rate, the first flow rate during the drawing responsive to expected or actual visibility within the surgical site (block 504); performing a surgical resection within the surgical site using the first instrument, the performing the surgical resection changes the first flow rate (block 506); and adjusting, by a fluid management system after the surgical resection, the first flow rate responsive to the expected or actual visibility within the surgical site (block 508). Thereafter, the method ends (block 510), likely to be immediately restarted.

Figure 6:
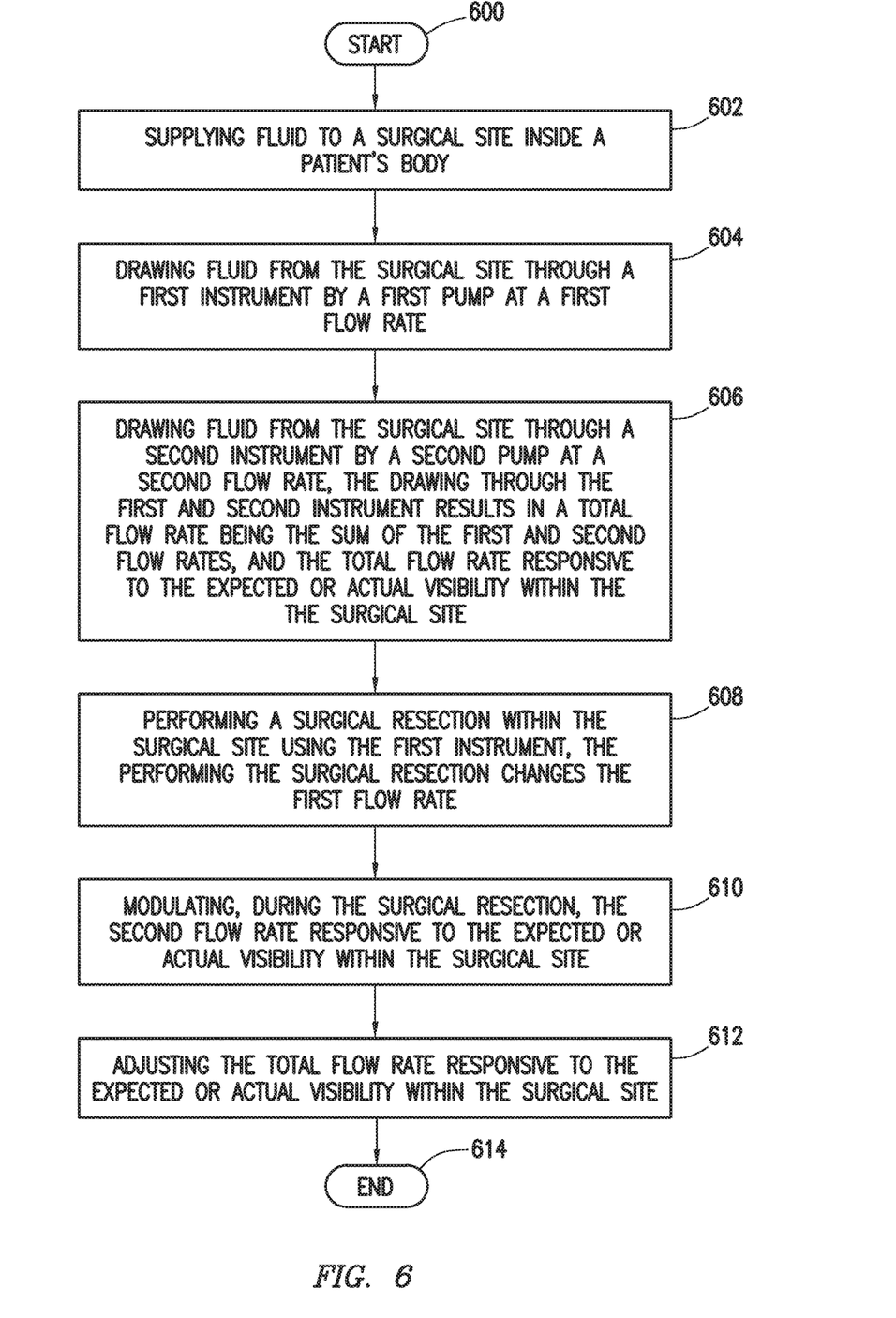
FIG. 6 shows a method in accordance with at least some embodiments.

FIG. 6 shows a method in accordance with at least some embodiments, at least a portion of which may be implemented using the fluid management system. In particular, the method starts (block 600) and proceeds to: supplying fluid to a surgical site inside a patient's body (block 602); drawing fluid from the surgical site through a first instrument by a first pump at a first flow rate (block 604); drawing fluid from the surgical site through a second instrument by a second pump at a second flow rate, the drawing through the first and second instrument results in a total flow rate being the sum of the first and second flow rates (block 606), and the total flow rate responsive to the expected or actual visibility within the surgical site; and then performing a surgical resection within the surgical site using the first instrument, the performing the surgical resection changes the first flow rate (block 608); modulating, during the surgical resection, the second flow rate responsive to the expected or actual visibility within the surgical site (block 610); and after the surgical resection, adjusting the total flow rate responsive to the expected or actual visibility within the surgical site (block 612). Thereafter, the method ends (block 614), likely to be immediately restarted.

Finally, a short discussion about the implementations of the instruments that make up the example systems. Referring again to FIG. 1, while possible that all the example instruments (e.g., the inflow cannula, the outflow cannula, the shaver, and the ablation device) may be separate components each inserted through separate apertures into the patient to reach the surgical site, in practice the cannulas may be defined by combined devices. For example, the inflow cannula, outflow cannula, and optics may be formed by use of an endoscope with a working channel and separate optics channel, and where the endoscope is telescoped within an external sheath. The inflow cannula may be the working channel of the endoscope, and the outflow cannula may be defined by inside diameter or inside surface of the sheath and an outside diameter of the endoscope. Moreover, a resection device itself sporting an internal channel (e.g., the shaver) may be telescoped through the working channel of the endoscope. Thus, inflow may be through the portion of the working channel not occupied by the resection device, the outflow cannula may be the space between the sheath and the endoscope, and the resection device itself defines the second outflow channel. In yet still other cases, the endoscope may define a working channel, a dedicated outflow channel, and a separate optics channel. Thus, the sheath may be omitted, and the endoscope may provide both the inflow cannula (through which the resection device may also be telescoped) and the outflow cannula. Other variations are possible, and one having ordinary skill, now understanding the various embodiments in view of this disclosure, could provide numerous alternative combinations of devices for providing the various cannulas by way of channels through various devices.

The above discussion is meant to be illustrative of the principles and various embodiments. For example, while the pumps associated with the instruments that provide outflow are shown as peristaltic pumps, any positive displacement pump may be used (e.g., gear pump, progressive cavity pump) such that the speed of the pump provides good knowledge of the flow through the pump. Also, non-positive displacement pumps (e.g., centrifugal pump) may be used in association with the instruments that provide outflow if the pumps are used in combination with fluid flow measurement devices (since flow through the pumps may be more dependent upon head pressure than speed of the pumps). Numerous variations and modifications will become apparent to those skilled in the art once the above disclosure is fully appreciated. It is intended that the following claims be interpreted to embrace all such variations and modifications.

What is claimed is:

1. A method comprising:
   supplying fluid to a surgical site inside a patient's body;
   drawing fluid from the surgical site through a first instrument by a first pump at a first flow rate; and then
   performing a surgical resection within the surgical site using the first instrument, the performing the surgical resection initially causes the first pump to draw the fluid at a second flow rate that is different from the first flow rate; and
   during or after the surgical resection, automatically adjusting, by a fluid management system, the first pump to draw fluid at a third flow rate that is different from the second flow rate, the third flow rate based at least on a type of surgical resection, an aggressiveness of the surgical resection, and at least one of:
   an amount of time of the surgical resection; and
   an amount of time since the surgical resection has ended.

2. The method of claim 1 wherein adjusting further comprises adjusting, by the fluid management system, without measuring actual visibility within the surgical site.

3. The method of claim 1 further comprising:
   prior to the adjusting, maintaining, by the fluid management system, the second flow rate for a predetermined period of time after the surgical resection has ended.

4. The method of claim 3 wherein the third flow rate is zero.

5. The method of claim 1 wherein automatically adjusting, by the fluid management system, the first pump to draw fluid at the third flow rate comprises pulsing the third flow rate.

6. The method of claim 1 wherein the first instrument is the only instrument providing outflow from the surgical site during the drawing, performing, and adjusting.

7. The method of claim 1 further comprising, prior to performing the surgical resection, drawing fluid from the surgical site through a second instrument by a second pump at a fourth flow rate, the drawing through the first and second instrument results in a first total flow rate being a sum of the first flow rate and the fourth flow rate, wherein the automatically adjusting comprises automatically adjusting both the first pump and the second pump to draw fluid from the surgical site at a second total flow rate that is the sum of the third flow rate and a fifth flow rate of the second pump, the fifth flow rate based on the type of the surgical resection, the aggressiveness of the surgical resection and at least one of: the amount of time of the surgical resection and the amount of time since the surgical resection has ended.

8. The method of claim 7 wherein performing the surgical resection further comprises initially modulating the fourth flow rate.

9. The method of claim 8 wherein initially modulating the fourth flow rate comprises causing the second pump to reduce to drawing fluid at a flow rate of zero.

10. The method of claim 7:
   wherein the second flow rate is higher than the first flow rate; and
   wherein the fifth flow rate is greater than the fourth flow rate; and
   after adjusting the second pump to draw fluid at the fifth flow rate, adjusting the second pump to draw fluid at sixth flow rate that is less than the fifth flow rate.

11. The method of claim 7 further comprising:
   detecting that the first instrument has been removed from operational relationship to the surgical site;
   causing the first pump to reduce to drawing fluid at a flow rate of zero responsive to detecting that the first instrument has been removed; and
   causing the second pump to draw fluid at a sixth flow rate, the sixth flow rate based on the type of the surgical resection, the aggressiveness of the surgical resection and at least one of: the amount of time of the surgical resection and the, amount of time since the surgical resection has ended.

12. The method of claim 1 wherein performing the surgical resection further comprises at least one selected from the group consisting of: operating the first instrument in the form of a mechanical resection device that draws tissue and fluid through the first instrument when resecting; and operating the first instrument in the form of an ablation device that ablates tissue and draws tissue and fluid through the first instrument when ablating.

13. The method of claim 1 wherein drawing further comprises drawing fluid from the surgical site through the first instrument by a first peristaltic pump.

14. The method of claim 1 wherein supplying fluid to the surgical site further comprises a selection from the group consisting of: supplying the fluid by gravity feed; supplying the fluid without the use of an inflow pump; pumping the fluid to the surgical site by a pump; pumping the fluid to the surgical site by a centrifugal pump; and pumping the fluid to the surgical site by a peristaltic pump.

15. The method of claim 1 wherein the surgical site is at least one selected from the group consisting of: a knee; a shoulder; a hip; an ankle; and a wrist.

16. The method of claim 1 further comprising measuring actual visibility within the surgical site, and wherein the third flow rate is based also on the actual visibility.

17. A system comprising:
a source of fluid configured to provide fluid to a surgical site inside a patient's body;
a first instrument fluidly coupled to the surgical site, the first instrument defines a first flow channel out which fluids flow from the surgical site;
a first pump system, a pump of the first pump system fluidly coupled to the first flow channel of the first instrument; and
a fluid management system communicatively coupled to the first pump system, the fluid management system having a controller configured to:
draw fluid from the surgical site through the first instrument by the first pump system at a first flow rate; and then
cause the first pump system to initially draw fluid from the surgical site at a second flow rate during periods of time when the first instrument performs surgical resection; and
adjust, during or after the surgical resection, the first pump to draw fluid at a third flow rate that is different from the second flow resection, an aggressiveness of the surgical resection, and at least one of:
an amount of time of the surgical resection; and
an amount of time since the surgical resection has ended.

18. The system of claim 17 wherein the controller is further configured to, prior to the adjustment, maintain the second flow rate for a predetermined period of time after the surgical resection has ended.

19. The system of claim 17 wherein the third flow rate is zero.

20. The system of claim 17 wherein when the controller adjusts the first pump to draw fluid at the third flow rate, the controller is configured to pulse the third flow rate.

21. The system of claim 17 wherein the first flow channel is the only flow channel within the surgical site, and the first flow channel is provided by an instrument that carries fluid out of the surgical site.

22. The system of claim 17 wherein the source of fluid further comprises fluid in a gravity feed configuration without a pump, and wherein when the controller adjusts, the controller is configured to adjust fluid flow through the surgical site without directly controlling fluid inflow to the surgical site.

23. The system of claim 17 wherein the first instrument is at least one selected from the group consisting of: a mechanical resection device in the form of shaver; a mechanical resection device in the form of a burr; and an ablation device.

24. The system of claim 17 further comprising:
a second instrument fluidly coupled to the surgical site, the second instrument defines a second flow channel out which fluids flow from the surgical site;
a second pump system distinct from the first pump system, a pump of the second pump system fluidly coupled to the flow channel of the second instrument; and
the fluid management system communicatively coupled to the second pump system, and the controller further configured to, during the surgical resection with the first instrument, cause the second rump system to modulate flow through the second flow channel of the second instrument at a fourth flow rate the fourth flow rate based on the t e of the surgical resection the aggressiveness of the surgical resection, and the amount of time of the surgical resection.

25. The system of claim 24 wherein the second instrument is at least one selected from the group consisting of: an outflow cannula; an outflow cannula defined by an inside surface of a sheath and an outside surface of an endoscope; an outflow cannula being the working channel of an endoscope; a mechanical resection device in the form of shaver; a mechanical resection device in the form of a burr; and an ablation device.

26. The system of claim 24 wherein when the controller modulates the flow through the second flow channel at the fourth flow rate, the controller causes the second pump system to reduce to drawing fluid at a flow rate of zero.

27. The system of claim 24:
wherein the second flow rate is higher than the first flow rate; and
wherein the fourth flow rate is greater than a fifth flow rate at which the controller causes the second pump system to draw fluid prior to the surgical reaction; and
the controller is configured to adjust the second pump system to draw fluid at a sixth flow rate after adjusting the second pump system to draw fluid at the fourth flow rate, the sixth flow rate being less than the fourth flow rate.

28. The system of claim 24 wherein the controller further configured to:
receive an indication that the first instrument has been removed from operational relationship to the surgical site;
cause the first pump system to reduce to drawing fluid at a flow rate of zero responsive to detecting that the first instrument has been removed; and
cause the second pump system to draw fluid at a sixth flow rate, the sixth flow rate based on the type of the surgical resection, the ac aggressiveness of the surgical resection, and at least one of: the amount of time of the surgical resection and the amount of time since the surgical resection has ended.

29. The system of claim 17 wherein the source of fluid further comprises at least one selected from the group consisting of: gravity feed from one or more saline bags; an inflow pump; an inflow pump being a centrifugal pump; and a peristaltic pump.

30. The system of claim 17 wherein the surgical site is at least one selected from the group consisting of: a knee; a shoulder; a hip; an ankle; and a wrist.

\* \* \* \* \*